United States Patent [19]

Keyes

[11] Patent Number: 5,370,638
[45] Date of Patent: Dec. 6, 1994

[54] OSTOMY POUCH

[75] Inventor: Denis E. Keyes, Rocky Hill, N.J.

[73] Assignee: E. R. Squibb & Sons, Inc., Princeton, N.J.

[21] Appl. No.: 994,757

[22] Filed: Dec. 22, 1992

[51] Int. Cl.$^5$ .............................................. A61F 5/44
[52] U.S. Cl. .................... 604/333; 55/385.4; 604/332
[58] Field of Search ............... 604/332, 333, 338, 342; 55/DIG. 12, 385.4

[56]  References Cited

U.S. PATENT DOCUMENTS

| | | | |
|---|---|---|---|
| 4,203,445 | 5/1980 | Jessup et al. | 604/333 |
| 4,274,848 | 6/1981 | La Gro | 604/333 |
| 4,460,392 | 7/1984 | Poulsen et al. | 604/333 |
| 5,579,658 | 4/1986 | Moller | 604/333 |

FOREIGN PATENT DOCUMENTS 3627980  6/1987  Germany ........................ 604/333

Primary Examiner—Jerome L. Kruter
Assistant Examiner—Rob Clarke
Attorney, Agent, or Firm—Stuart E. Krieger

[57]  ABSTRACT

The ostomy pouch is formed of a flexible plastic material with a waste inlet opening and a gas outlet opening proximate the waste inlet opening. The gas outlet opening is of a configuration and size that resists entry of outside water into the pouch through the gas outlet opening. A filter aligned with the gas outlet opening is bonded at a peripheral zone surrounding the gas outlet opening, leaving an unbonded area that communicates with the gas outlet opening. A free face of the filter is gas impermeable. Gases within the pouch pass through an exposed, gas permeable peripheral edge of the filter toward the center and exit into the unbonded section for evacuation through the gas outlet opening.

9 Claims, 2 Drawing Sheets

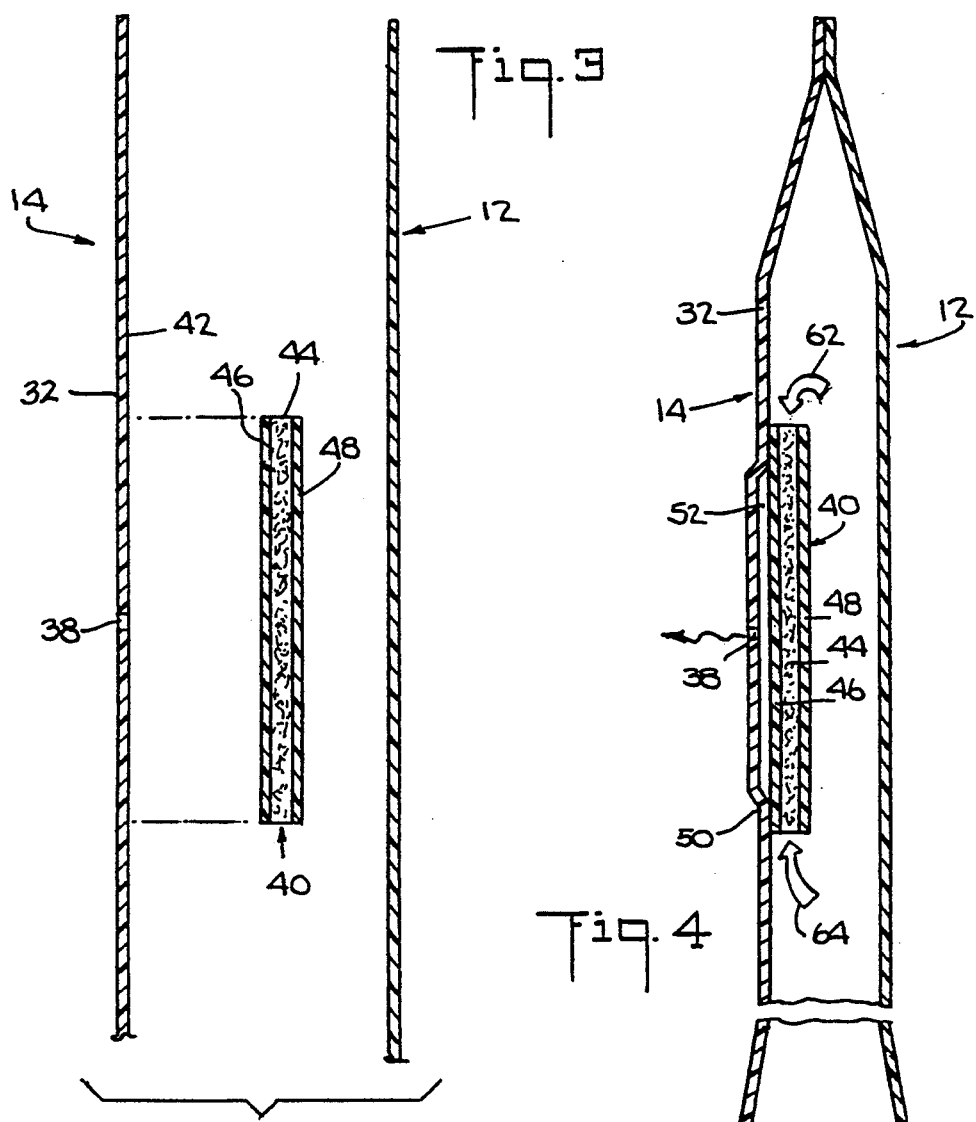

OSTOMY POUCH

BACKGROUND OF THE INVENTION

This invention is directed to ostomy pouches and more particularly to an ostomy pouch having a gas evacuation system that resists entry of outside water into the pouch.

Gases emitted from the stoma into an ostomy pouch and gases that issue from waste material collected in an ostomy pouch are usually evacuated through a deodorizing filter. A gas outlet is thus provided in the ostomy pouch, normally adjacent the filter to ensure that the outward flow of gas passes through the filter. Thus the term "gas" as used herein is intended to refer to gas from the stoma and gas from waste material collected in an ostomy pouch.

Although gas outlets in an ostomy pouch perform an essential function, they can also allow outside water to enter the pouch, especially when an individual swims or showers. Thus some ostomy pouches include sealing devices to temporarily cover a gas outlet while an individual swims or showers.

One problem in providing a temporary seal for a gas outlet in an ostomy pouch is that the seal may not be conveniently available during a time of need, thus discouraging an individual from exposure to water. A further problem is that a user may forget to remove a temporary seal, resulting in overexpansion of the pouch by unevacuated gas.

In some instances, removal of a temporary seal from a gas outlet can stretch the area around the outlet and cause inadvertent enlargement of the outlet. If an enlarged gas outlet permits a greater than optimum flow of gas out of the ostomy pouch, there may be insufficient deodorization of the evacuated gases.

It is thus desirable to provide an ostomy pouch with a gas evacuation system that requires no special shielding or protection to prevent outside water from entering the pouch.

OBJECTS AND SUMMARY OF THE INVENTION

Among the several objects of the invention may be noted the provision of a novel ostomy pouch having a novel gas evacuation system that resists entry of outside water into the pouch, a novel ostomy pouch having a gas outlet that is configured to prevent outside water from entering the pouch, a novel ostomy pouch having a gas outlet that is sized to permit evacuation of gas from the pouch yet resists entry of outside water into the pouch, a novel ostomy pouch having a gas evacuation opening that does not require shielding or closure to prevent outside water from entering the pouch through the opening, and a novel method of preventing outside water from entering an ostomy pouch.

Other objects and features of the invention will be in part apparent and in part pointed out hereinafter.

In accordance with a preferred embodiment of the invention, the ostomy pouch includes an envelope formed of flexible plastic material that is substantially impervious to body waste material including liquids and gases. The pouch is formed with a waste inlet opening near the top end portion and further includes a gas outlet spaced from the waste inlet opening.

The gas outlet is formed as an evacuation opening with a diameter in the range of approximately 0,035 to 0,045 inches. The gas outlet is backed up by a deodorizing filter for deodorizing gases produced by waste material in the pouch and/or gases entering the pouch through the stoma.

An annular peripheral portion of the deodorizing filter is joined to an inner surface of the pouch and defines an unbonded circular area that aligns with the evacuation opening. The deodorizing filter has opposite face cover portions that sandwich filtration material. One of the face covers is a gas impermeable layer and the other a gas permeable layer. The gas impermeable cover layer faces the inner chamber of the pouch whereas the gas permeable cover layer faces a wall portion of the pouch containing the evacuation opening.

Under this arrangement, gas within the pouch can only enter the filter at the periphery of the filtration material. Gas thus flows on a radial path through the filter and exits through the gas permeable cover layer into the unbonded area between the gas permeable cover layer and the wall of the pouch for evacuation through the gas outlet opening.

In instances where outside water comes in contact with the pouch during showering or swimming, for example, it is unable to pass through the gas outlet opening because of surface tension. Thus there is no need to cover or otherwise shield the gas outlet opening when an individual showers or swims.

The invention accordingly comprises the constructions and method hereinafter described, the scope of the invention being indicated in the claims.

DESCRIPTION OF THE DRAWINGS

In the accompanying drawings,

FIG. 3 is an enlarged, exploded, fragmentary sectional view thereof;

FIG. 4 is a sectional view thereof, taken on the line 4—4 of FIG. 1; and,

FIG. 5 is an enlarged fragmentary sectional detail thereof.

Corresponding reference characters indicate corresponding parts throughout the several views of the drawings.

DETAILED DESCRIPTION OF THE INVENTION

Figure 1:
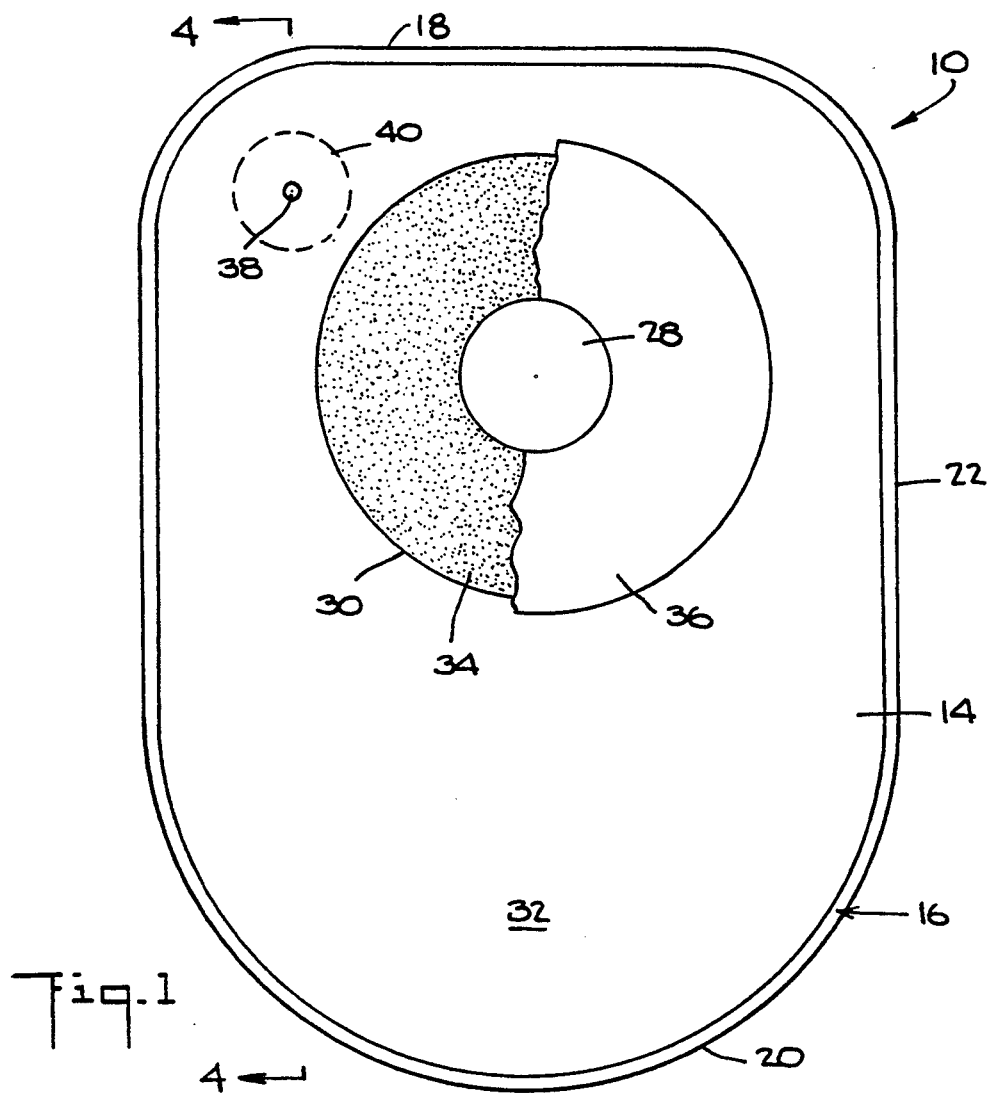
FIG. 1 is a simplified schematic plan view of an ostomy pouch incorporating one embodiment of the invention.
Figure 2:
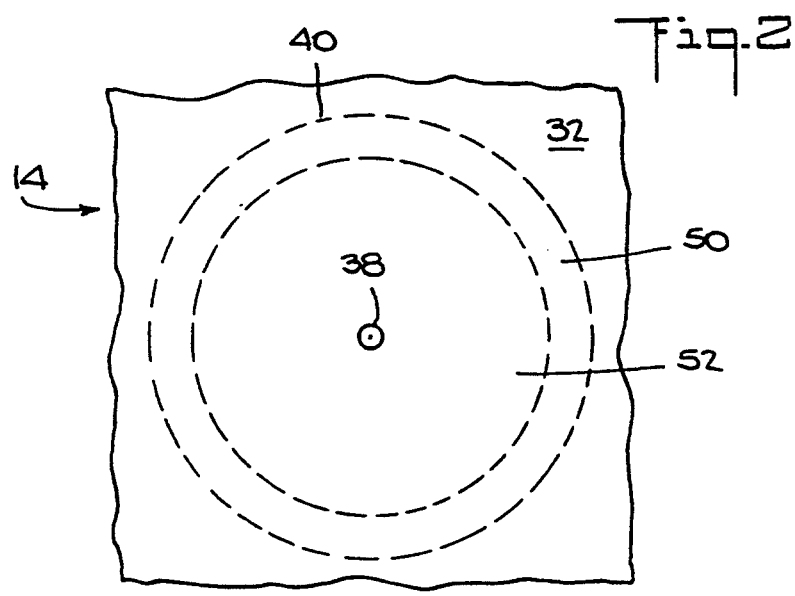
FIG. 2 is an enlarged fragmentary detail thereof.

An ostomy pouch incorporating one embodiment of the invention is generally indicated by the reference number 10 in FIG. 1. The ostomy pouch is formed of a suitable known thermoplastic material that is gas impermeable, flexible and expandable.

The pouch 10 includes a front wall portion 12 that faces away from the abdomen and a rear wall portion 14 that confronts the abdomen, joined together by a peripheral thermo-weld 16. The wall portions 12 and 14 are approximately 40 to 100 microns thick. The pouch 10 further includes a top end portion 18, a bottom end portion 20 and opposite side portions 22 and 24.

A stoma engagement opening 28 is formed in the rear wall portion 14 nearer the top end 18 of the pouch 10 than the bottom end portion 20. The engagement opening 28 is bordered by a known flexible plastic coupling ring 30 bonded to an outside surface 32 of the rear wall portion 14. An exposed face 34 of the coupling ring 30 is coated with a known contact adhesive such as Stomahesive ® sold by ConvaTec. The coupling ring 30 permits adhesion of the pouch 10 to the abdominal area surrounding the stoma (not shown). A disposable release cover 36 is releasably secured to the adhesive layer 34 on the coupling ring 30 for removal before use of the pouch 10.

A gas evacuation opening 38 is provided in the rear wall portion 14 of the ostomy pouch 10, offset from the stoma engagement opening 28 and beyond the periphery of the coupling ring 30 near the top and side edges 18 and 24. The gas evacuation opening 38 is approximately 0.035 to 0.045 inches in diameter. Preferably the opening 38 is made by piercing the rear wall portion 14. Thus no material is removed.

A generally circular deodorizing filter 40, of the type sold under the designation Freudenberg Code 9347 by Freudenberg Industrial of West Yorkshire, England, is provided at an inside surface 42 of the rear wall portion 14 such that the center of the filter 40 is substantially aligned with the gas evacuation opening 38. The filter 40 includes a filtration layer 44 formed of polyurethane foam containing activated carbon sandwiched between cover layers 46 and 48. The layer 46 is gas permeable and formed of Lutravil VP708T Microfine, for example, whereas the layer 48 is gas impermeable and formed of microporous film that functions as a barrier to the passage of waste gas. Preferably the filter 40 is approximately 24.4 mm.±1 mm. in diameter and 2 to 3 mm. thick.

The filter 40 is joined to the inside surface 42 of the rear wall portion 14 at a peripheral bonding zone 50 of the cover layer 46. Any suitable known hot melt adhesive can be used to provide the bond at the bonding zone 50 with the bond width preferably approximately 8.6 mm. Thus a circular unbonded area 52 of approximately 7.1 mm in diameter is defined on the cover layer 46 within the confines of the bonding zone 50. The unbonded area 52 is adjacent to and surrounds the evacuation opening 38 at the inside surface 42 of the rear wall portion 14.

In using the ostomy pouch 10, the release cover 36 is peeled from the coupling ring 30 to expose the adhesive surface 34. The pouch 10 is then secured at the coupling ring 30 to the abdominal area surrounding the stoma. Gases emitted from the stoma into the chamber 54 of the pouch 10 and gases that issue from waste material 56 collected in the pouch 10 build up to a predetermined pressure within the pouch chamber 54.

Since the cover layer 48 of the filter 40 is gas impermeable, gases confined in the pouch chamber 54 enter the filtration layer 44 at the periphery in the directions indicated by the arrows 62 and 64 in FIG. 4. The gases then flow radially through the filter 40 toward the center and pass through the gas permeable layer 46 into the unbonded area 52 for evacuation through the gas evacuation opening 38.

It has been found that the configuration of the gas evacuation opening 38 as an opening of 0.035 to 0.045 inches in diameter on the rear wall portion of the pouch 10 is sufficient to maintain a predetermined gas evacuation flow rate that permits gases passing through the filter 40 to become sufficiently deodorized by the filter 40 before they pass into the unbonded section 52 for evacuation through the gas evacuation opening 38.

It has been found that an individual can shower, bathe or swim while using the pouch 10 without water intrusion into the evacuation opening 38.

Thus the predetermined size range of the evacuation opening, namely the 0.035 to 0.045 inch diameter, will resist the entry of water outside the bag into the bag through the evacuation opening 38 because of surface tension, even without shielding or otherwise covering the opening 38.

Although the filter and gas outlet are shown in an ostomy pouch having an adhesive coupling to the abdominal area surrounding the stoma, the same arrangement can be used on pouches which have a mechanical coupling that interlocks to a mating coupling provided on the area around the stoma.

Some advantages of the invention evident from the foregoing description include an ostomy pouch that allows the user freedom to shower or swim without the need to go through special preparations to protect a gas evacuation system in the ostomy pouch from outside water.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. An ostomy pouch for holding body waste passing through a stoma comprising,
   a) an envelope formed of a flexible plastic material defining a collection chamber for body waste, said envelope being substantially impervious to said body waste including solids, liquids and gases,
   b) said envelope having a top end portion and a bottom end portion and being formed with a waste inlet opening proximate said top end portion, said waste inlet opening being of predetermined size and including means for fitting said opening around a stoma when said pouch is operational such that said collection chamber is substantially leak tight in the area around said waste inlet opening,
   c) said envelope being further formed with a gas outlet opening spaced from said waste inlet opening and proximate said top end portion, said envelope being otherwise sealed to prevent leakage of body waste from said collection chamber when said pouch is operational, said gas outlet opening being of a predetermined size having a diameter in the range of 0.035 to 0.045 inches to resist entry of outside water into said collection chamber through said outlet opening when said pouch is operational,
   d) a filter for deodorizing gaseous waste including gases produced by the waste material in said collection chamber and gases passing into said collection chamber from said stoma, said filter being joined to said envelope in alignment with said gas outlet opening such that gaseous waste within said bag must pass through said filter before exiting from said bag through said gas outlet opening when said pouch is operational,
   e) said envelope having an inner surface, said filter having a gas permeable cover layer bonded to the inner surface of said envelope along a bonding zone that surrounds said gas outlet opening, said gas permeable cover layer having an area that is unbonded to said envelope within the confines of said bonding zone, said unbonded area being in alignment with said gas outlet opening such that gas passing through said filter and said gas permeable cover layer is directed to the unbonded area of said filter to permit said gas to exit from said envelope through said gas outlet opening.

2. An ostomy pouch as claimed in claim 1 wherein said gas outlet opening is offset from said waste inlet opening.

3. An ostomy pouch as claimed in claim 1 wherein said envelope includes a first wall portion adapted to confront said abdomen, said waste inlet opening and said gas outlet opening being formed in said first wall portion.

4. An ostomy pouch as claimed in claim 1 wherein said filter is in the shape of a circular disk and the bonding zone is at a predetermined peripheral portion of said filter, and said unbonded area is a predetermined circular area surrounded by said bonding zone.

5. An ostomy pouch as claimed in claim 1 wherein said filter includes a filtration layer sandwiched between a gas impermeable cover layer and said gas permeable cover layer such that the periphery of said filtration layer is exposed such that gas passing through said filter from said collection chamber enters said filter at said exposed peripheral edge of said filtration layer and exits said filter through the unbonded area of said gas permeable cover layer for evacuation through said gas outlet opening.

6. An ostomy pouch as claimed in claim 5 wherein said filter is aligned with said outlet opening such that said outlet opening is approximately at the center of said filter.

7. A method of preventing outside water from entering an ostomy pouch comprising,
   a) forming a gas outlet opening and a waste inlet opening on a wall of the pouch that confronts the abdomen,
   b) sizing the gas outlet opening in the range of 0.035 to 0.045 inches in diameter,
   c) bonding a deodorizing filter to the pouch in alignment with the gas outlet opening by using a peripheral bond to provide a central area of the filter that is not bonded to the pouch,
   d) covering a free face of the filter with a gas impermeable cover layer,
   e) exposing a peripheral edge of the filter to permit entry of gas into the filter only at the peripheral edge, and exit at the unbonded area for evacuation through the outlet opening.

8. The method of claim 7 including covering the face of the filter that contacts the pouch with a gas permeable cover layer.

9. The method of claim 7 wherein the gas outlet opening is formed by piercing the pouch wall without removing material from the pouch wall.

* * * * *